United States Patent [19]

Sherwin et al.

[11] Patent Number: 4,995,392
[45] Date of Patent: Feb. 26, 1991

[54] SELF-PREPARING ELECTRODE WITH REMOVABLE PLASTIC ABRADING BRUSH

[75] Inventors: Gary W. Sherwin, South Huntington Township, Westmoreland County; Edward E. Kovach, Penn Hills; Albert L. Schmidt, Murrysville, all of Pa.

[73] Assignee: Westinghouse Electric Corp., Pittsburgh, Pa.

[21] Appl. No.: 290,390

[22] Filed: Dec. 29, 1988

[51] Int. Cl.$^5$ .............................................. A61B 5/04
[52] U.S. Cl. .................................................. 128/639
[58] Field of Search ................................ 128/639–641

[56] References Cited

U.S. PATENT DOCUMENTS

| | | | |
|---|---|---|---|
| 3,774,592 | 11/1973 | Lahr | 128/640 |
| 4,311,152 | 1/1982 | Modes et al. | 128/641 |
| 4,583,547 | 4/1986 | Granek et al. | 128/639 |
| 4,632,120 | 12/1986 | Sherwin et al. | 128/639 |
| 4,640,290 | 2/1987 | Sherwin | 128/642 |
| 4,706,679 | 11/1987 | Schmidt et al. | 128/639 |
| 4,709,202 | 11/1987 | Sherwin | 128/644 |

Primary Examiner—Lee S. Cohen
Assistant Examiner—David Shay
Attorney, Agent, or Firm—John K. Williamson

[57] ABSTRACT

A self-preparing electrode includes a conductive conical disk and a nonconductive plastic abrading brush removably interfitted through an aperture in the disk. The brush extends axially through the disk cavity to an abrading end of the brush disposed beyond the cavity at the large diameter end of the disk. The brush also extends axially through and beyond the aperture of the disk to a fused end of the brush which holds the strands or bristles of the brush together. An apparatus which fabricates the brush and assembles it to an electrode disk uses a pair of pressure roller to feed multiple strands from supply spools mounted in a supply rack, through input and output tubular orifices, to and through the aperture of the disk. A shuttle positions a fusing anvil in contact with the leading ends of the strands extending through the disk aperture for fusing them into a connecting bead. A cutting blade is then employed to sever the strands a short distance from the disk to finish forming the brush and define an abrading end thereon.

9 Claims, 4 Drawing Sheets

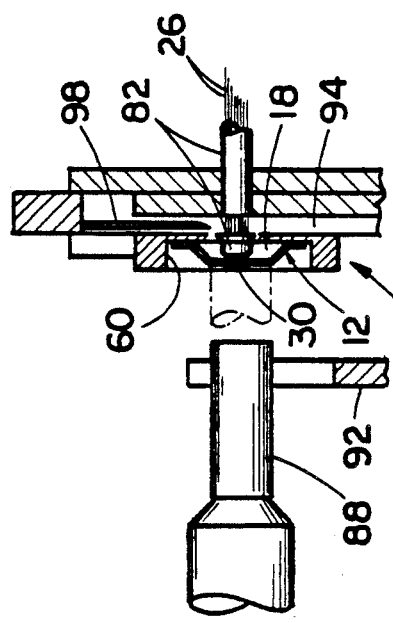
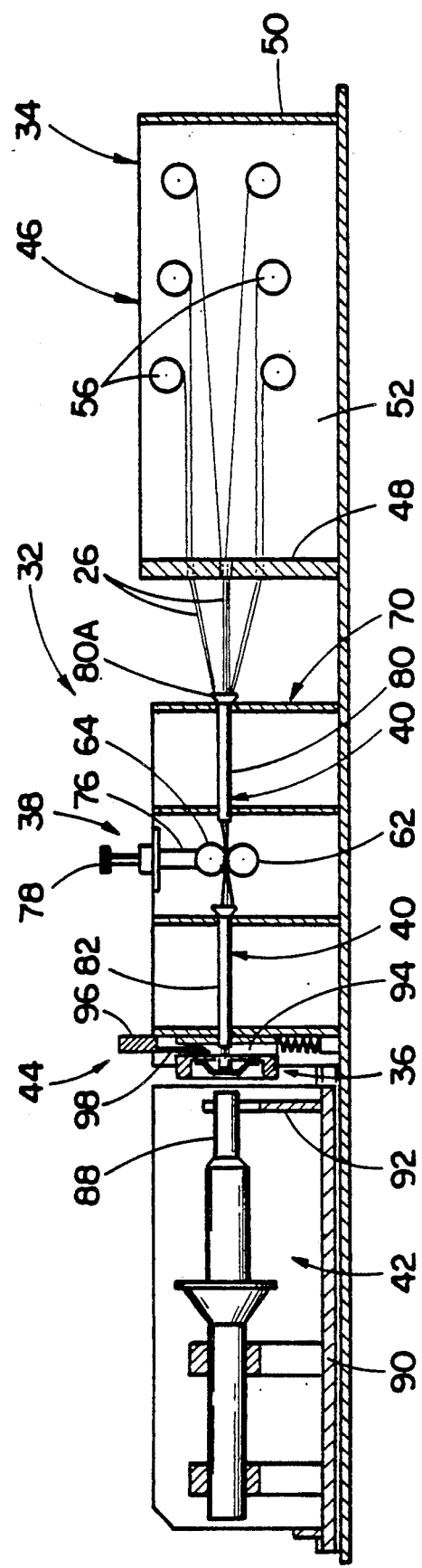
FIG. 3A
FIG. 3

SELF-PREPARING ELECTRODE WITH REMOVABLE PLASTIC ABRADING BRUSH

BACKGROUND OF THE INVENTION

1. Field of the Invention

The present invention relates generally to electrodes for sensing the electrical potential of a person's skin and, more particularly, is concerned with an electrode having a removable nonconductive plastic abrading brush and with a method and apparatus for assembling the same.

2. Description of the Prior Art

Electroencephalograms (EEG) and electrocardiograms (EKG) are commonly performed on medical patients by sensing the electrical potential of skin covering the brain and heart, respectively. The skin potential is sensed by use of conductive elements called probes, monitors or electrodes. One or more electrodes are placed in electrical contact with the blood-rich epidermis layer of skin.

One standard electrode used is composed of silver metal and takes the form of a hollow, frusto-conical shaped disc. The disc-shaped electrode defines an open cavity for receiving an electrolyte cream. A hole is provided in the electrode for injecting a supplemental quantity of the electrolyte cream into the cavity if needed. A conductor is attached to the electrode and the electrolyte cream provides a conductive coupling between the skin and the electrode.

The standard electrode is not self-preparing, that is, it cannot be used just by being place against the person's skin. Instead, before the electrode is applied to the person's skin, the location on the skin where it will be applied must be prepared by shaving the hair so that then the skin can be abraded with an abrading tool or an abrading grit-bearing electrolyte cream to remove the outer dead skin layer and facilitate making electrical contact by the electrode with the blood-rich epidermis skin layer.

In medical applications which are typically carried out by skilled personnel, the shaving and abrading procedures can be performed rather quickly. Increasingly, EEG measurements also have non-medical applications. However, in non-medical applications EEG measurements are typically carried out by unskilled personnel. The above-outlined skin preparation procedures are time-consuming and generally unacceptable for persons involved in non-medical applications.

Recently, an electrode incorporating a conductive brush has been devised which is characterized as self-preparing. It is disclosed in U.S. Pat. No. 4,706,679 to Schmidt et al which is assigned to the same assignee as the present invention. Its use does not require shaving of the hair from the skin at the location where the electrode is to be applied. Abrading is accomplished by the tips of the bristles of the brush which when pressed against the skin penetrate or abrade through the dead layer of skin. The conductive brush bristles or strands being composed of silver metal maintain electrical contact with the skin. This conductive brush electrode can be applied in a few seconds compared to fifteen to thirty minutes for the standard electrode.

However, problems have been encountered in the use of this conductive brush electrode in measurement of transient evoked potentials. Steady state fields develop around the conductive bristles or strands. Ion concentrations develop near the end or tip points of the brush strands causing interference with measurements.

Consequently, a need exists for another approach to providing a self-preparing electrode which will overcome the problems encountered with the recent conductive brush electrode without returning to the earlier time-consuming preparation procedures.

SUMMARY OF THE INVENTION

The present invention provides a self-preparing electrode designed to satisfy the aforementioned needs. The electrode includes a conductive conical disk preferably composed of silver metal and a nonconductive abrading brush preferably composed of a plastic monofilament and being removably interfitted through an aperture in the disk. The removable nature of the brush allows it to be discarded after a single use and the silver disk to be reused by fabrication and insertion of another brush. The nonconductive nature of the brush eliminates the ion concentration problem associated with the prior conductive brush. A low cost plastic material can be used for construction of the nonconductive plastic abrading brush in place of more expensive silver metal in the prior conductive brush. However, the nonconductive plastic abrading brush retains the self-preparing nature of the prior conductive brush.

The present invention also provides a method and apparatus for assembling the electrode with the nonconductive plastic abrading brush. Initially, the nonconductive plastic brush was assembled manually by hand-tying bunched strands together. This was time-consuming and required post-assembly sterilization of the brush to eliminate potential contamination from manual handling. Automated assembly of the brush has overcome these drawbacks of the nonconductive plastic brush. Assembly time has been reduced from one-half hour for manual assembly to a just few seconds for automated assembly. Contamination has been avoided and the need for post-assembly sterilization eliminated.

Accordingly, the present invention is directed to a self-preparing electrode which comprises: (a) a conductive disk having a central aperture; and (b) a nonconductive multi-strand abrading brush removably mounted through the aperture in the disk. The disk defines a hollow cavity for receiving and holding an electrolyte cream for providing an electrically conductive coupling between the disk and a person's skin. The cavity in the disk is open at its forward large diameter end and closed at its opposite rearward small diameter end except for the aperture. The brush extends axially through the cavity to an abrading end of the brush which is disposed beyond the open forward end of the cavity and to an opposite fused end of the brush which is disposed through and beyond the aperture in the disk.

The present invention is also directed to a method and apparatus for assembling the self-preparing electrode which comprises the operative steps of: (a) supplying a plurality of strands of brush bristle and collecting the strands together at one end of a plurality of side-by-side parallel paths; (b) supporting an electrode disk having a central aperture therethrough at an opposite end of the paths; (c) feeding the strands along the paths; (d) guiding the strands along the paths toward the electrode disk to insert leading ends of the feeding strands through the aperture of the electrode disk; (e) fusing together the leading ends of the strands once inserted through the electrode disk aperture to define one end of a multi-strand brush removably attached to the disk; and (f) severing the strands at a location spaced from their fused-together leading ends and displaced beyond the disk to define an opposite abrading end of the brush.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the course of the following detailed description, reference will be made to the attached drawings in which:

FIG. 3 is an elevational view of the apparatus as seen along line 3—3 of FIG. 2.

FIG. 3A is an enlarged view of the circled portion of the apparatus of FIG. 3.

DETAILED DESCRIPTION OF THE INVENTION

Figure 1:
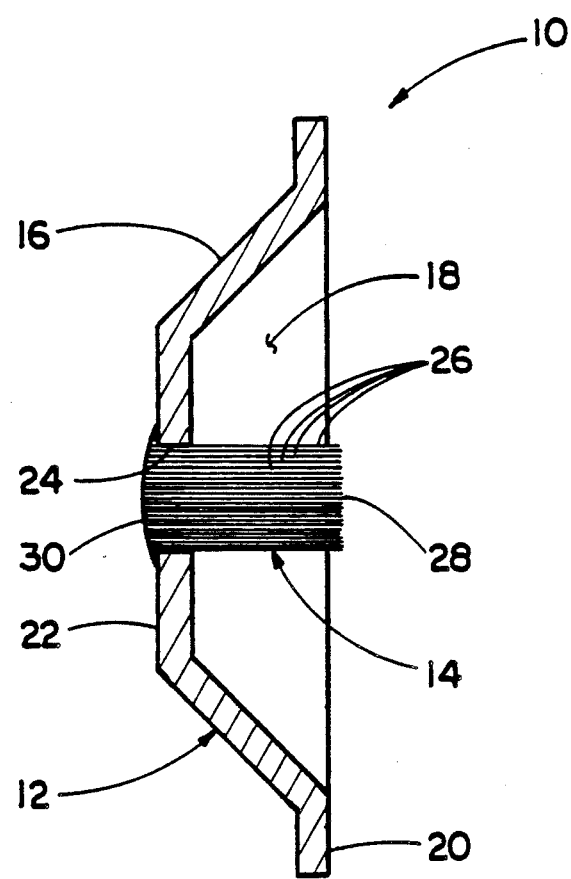
FIG. 1 is a vertical sectional view of the self-preparing electrode of the present invention.
Figure 2:
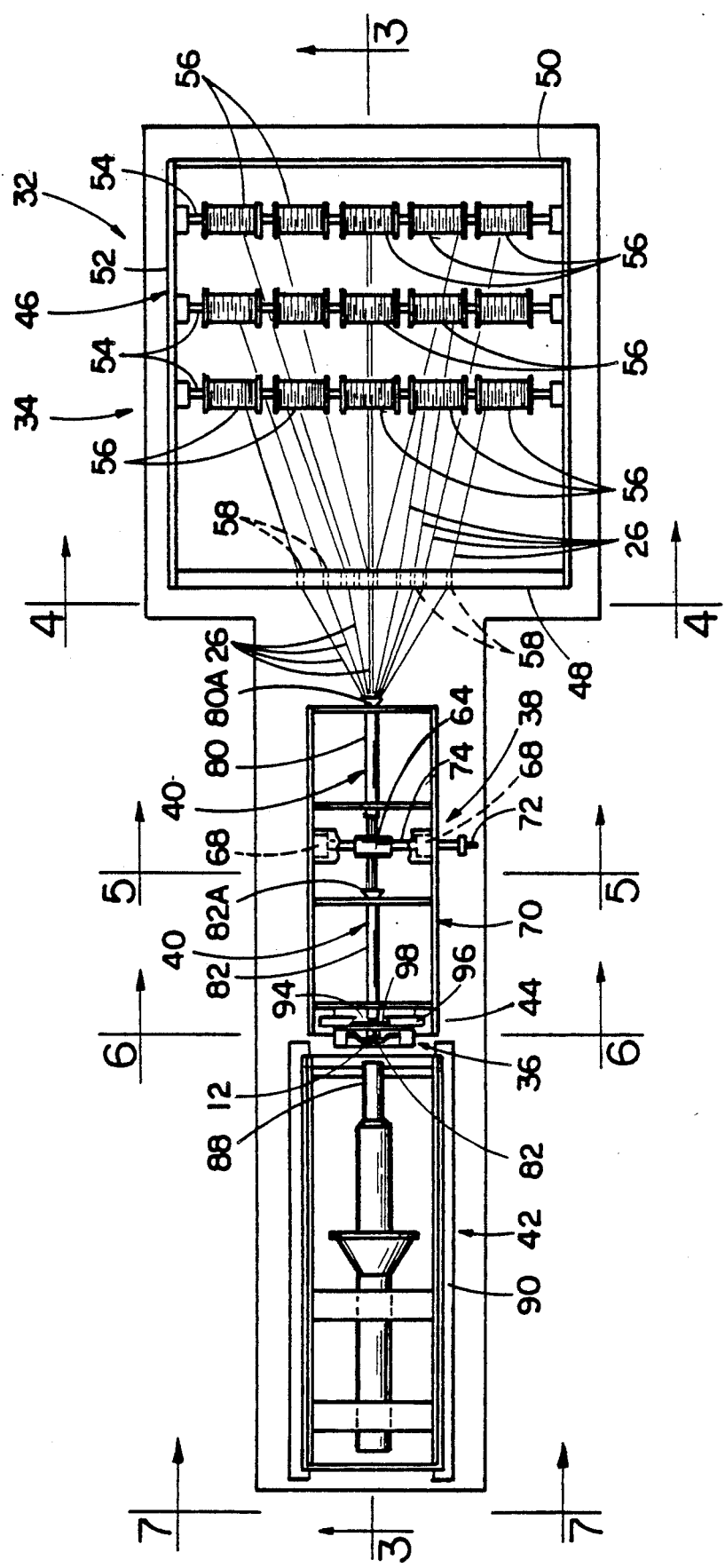
FIG. 2 is a top plan view of the apparatus of the present invention for assembling the electrode of FIG. 1.
Figure 4:
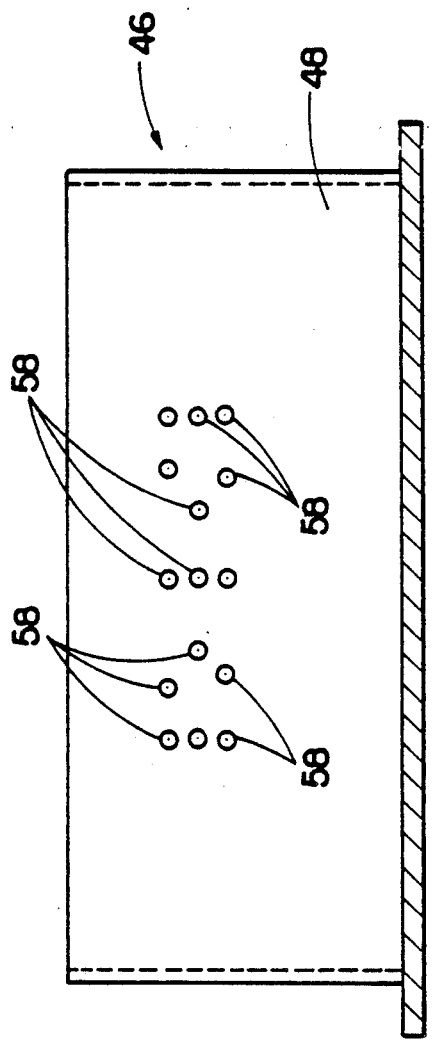
FIG. 4 is an enlarged view of a multi-strand supply of the apparatus as seen along line 4—4 of FIG. 2.
Figure 5:
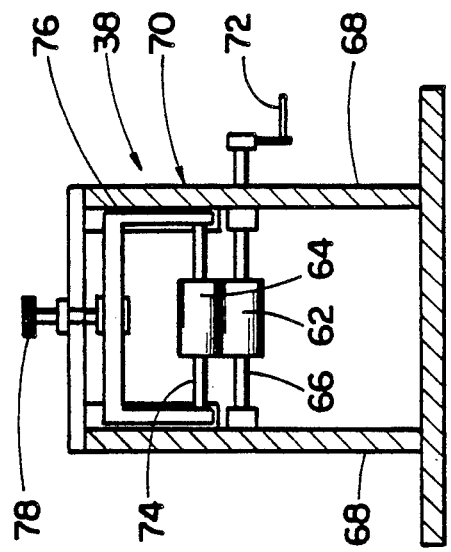
FIG. 5 is an enlarged view of a strand feeding mechanism of the apparatus as seen along line 5—5 of FIG. 2.
Figure 7:
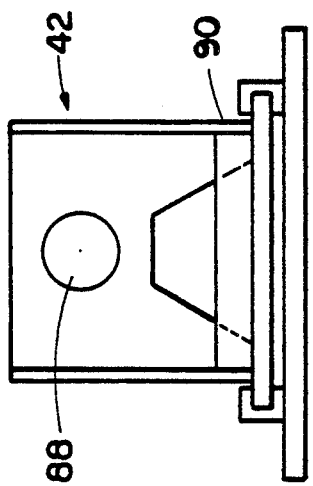
FIG. 7 is an enlarged view of a strand fusing mechanism of the apparatus as seen along line 7—7 of FIG. 2.

In the following description, like reference characters designate like or corresponding parts throughout the several views of the drawings. Also in the following description, it is to be understood that such terms as "forward", "rearward", "left", "right", "upwardly", "downwardly", and the like, are words of convenience and are not to be construed as limiting terms.

Self-Preparing Electrode of Present Invention

Referring now to the drawings, and particularly to FIG. 1, there is shown a self-preparing electrode, generally designated by the numeral 10, for use primarily with equipment making EEG and EKG measurements and being constructed in accordance with the principles of the present invention. Basically, the self-preparing electrode 10 includes a conductive disk 12 and a nonconductive multi-strand abrading brush 14.

The disk 12 of the electrode 10 has a frusto-conical flared continuous side wall 16 defining a hollow cavity 18 for receiving and holding an electrolyte cream (not shown) for providing an electrically conductive coupling between the disk 12 and a person's skin. The disk 12 also has an annular front flange 20 merging from the side wall 16 and extending radially outwardly about the large diameter front end thereof where the front of the cavity 18 in the disk 12 is open. Further, the disk 12 has a planar rear end wall 22 merging with the side wall 16 at its small diameter rear end and closing the rear of the cavity 18 except for a circular aperture 24 defined centrally through the rear end wall 22. The disk 12 is preferably composed of silver metal, although other conductive materials can be used.

The brush 14 of the electrode 10 is composed of a plurality of elongated strands 26 which are bunched and held together side-by-side to form of bundle of short, and relatively stiff, bristles. By way of example, thirty of the strands 26 can compose the brush 14. The brush 14 has a forward abrading end 28 defined by the bare tips of the strands 26. The brush 14 also has an opposite end 30 in which the opposite ends of the strands are fused together to form a connecting bead 30 which holds the strands together in the bunched or bundled relationship. By way of example, the abrading brush 14 can be composed of a plastic monofilament such as a conventional fish line, although other nonconductive materials can be used.

The brush 14 is removably mounted or interfitted through the aperture 24 in the disk 12. The aperture 24 is sized relative to the diameter of the brush 14 to provide a tight squeezing or frictional fit of the brush through the aperture in the rear end wall of the disk 12. The brush 14 is thus mounted to extend axially through the cavity 18, terminating at its forward abrading end 28 which is disposed beyond the front of the cavity 18 and at its opposite fused beaded end 30 which is disposed through and beyond the aperture 24 in the disk rear end wall 22. When the electrode 10 is applied, contact is initially made by the forward-projecting abrading end 28 of the brush 14 for penetrating the dead skin so that the electrolyte cream carried in the cavity of the disk 12 about the brush 14 can electrically couple with the skin. After the brush 14 has completed its function of abrading the dead surface skin, the brush 14 either is retracted by the operator pulling rearwardly on its exposed rear beaded end 24 until its forward abrading end 28 no longer projects beyond the front flange 20 of the disk 12 or is removed entirely by the operator since it no longer serves any purpose.

Electrode Assembling Apparatus of Present Invention

Turning now to FIGS. 2–7, there is illustrated an apparatus of the present invention, generally designated by the numeral 32, for fabricating the nonconductive plastic abrading brush 14 and for assembling the brush 14 to the conductive disk 12 to form the self-preparing electrode 10 of FIG. 1. In its basic components, the assembling apparatus 32 includes a multi-strand supply 34, an electrode disk support 36, a strand feeding mechanism 38, a stand guide 40, a strand fusing mechanism 42, and a strand severing mechanism 44.

The multi-strand supply 34 of the apparatus 32 includes a generally rectangular stock supply rack 46 having vertical front and rear walls 48,50 and vertical opposite side walls 52 extending between and interconnecting the front and rear walls. A plurality of elongated rods 54 extend between and are mounted to the side walls 52 of the supply rack 46. The rods 54 rotatably mount a plurality of rows of spools 56 from which are supplied a plurality of strands 26 of brush bristle. There is one spool 56 for each bristle of the brush 14 being formed. A tension string (not shown) rubs on each spool 56 to prevent the spools from fouling with each other. The front wall 48 of the supply rack 46 has a pattern of small holes 58 (see FIG. 4) which route the multiple strands 26 from the respective spools 56 toward the feeding mechanism 38 and strand guide 40 for collecting the strands 26 together at one end of a plurality of side-by-side parallel paths defined through the apparatus 32.

The electrode disk support 36 of the apparatus 32 is provided at the opposite ends of the strand paths. The support 36 is an upright member having a detent or countersink 60 formed therein which receives the electrode disk 12 as shown generally in FIG. 3 and more clearly in FIG. 3A. The strand feeding mechanism 38 and strand guide 40 are located between the multi-strand supply 34 and the disk support 36.

The feeding mechanism 38 of the apparatus 32 includes a pair of lower and upper pressure rollers 62,64 which are preferably rubber-coated for gripping the strands therebetween. The lower roller 62 is mounted on a shaft 66 extending and journalled between a pair of upright members 68 of a frame structure 70. A handle 72 can be provided on one end of the shaft 66 for use in manually rotating the lower roller 62. Alternatively, the lower roller 62 can be driven by a motor. The upper roller 66 is mounted on a shaft 74 which, in turn, is rotatably mounted to a support mechanism 76 operable by turning an adjustment knob 78 for vertically varying the position of the upper roller 64 toward and away from the lower roller 62 for adjusting the contact pressure between the rollers.

The strand guide 40 of the apparatus 32 includes input and output tubular orifices 80,82 disposed on opposite ends of the feeding mechanism rollers 62,64 and axially aligned with one another. The orifices 80,82 receive and guide the strands 26 along the parallel paths into and from the feeding mechanism 38 and toward the electrode disk 12 at the disk support 34. The input orifice 80 has a flared entry end 80A for receiving and converging the strands 26 into a tight cylindrical bundle and directing them along the paths toward and between the lower and upper feeding rollers 62,64. Passage of the stands 26 between the rollers 62,64 tends to flatten the bundle of strands into a planar configuration. As they feed through the flared entry end 82A of the output orifice 82, the strands recollect into a cylindrical configuration from the generally planar configuration they assumed in passing between the feeding rollers 62,64. The exit end 82B of the output orifice 82 extends through the countersink 60 of the disk support 36 and is disposed adjacent the aperture 24 in the electrode disk 12 for facilitating ease of insertion of the leading ends of the strands 26 therethrough.

The strand fusing mechanism 44 of the apparatus 32 includes a fusing anvil 88 mounted on a shuttle 90 which, in turn, is mounted for reciprocatory sliding movement toward and away from the electrode disk support 36 on the side thereof opposite from the strand guide 40. The shuttle 90 also supports and positions a hold-down saddle 92. The shuttle 90 is initially disposed in the position shown in FIGS. 2 and 3 wherein the fusing anvil 88 is spaced from the electrode disk support 36 allowing insertion of a disk 12 into the countersink 60. When the shuttle 90 is moved toward the right in FIGS. 2 and 3, it places the fusing anvil 88 in a forward position for contact with the leading ends of the strands 26 once they are inserted through the disk aperture 24. Simultaneously, the hold-down saddle 92 engages the disk 12 for holding it in the proper position for the strand leading ends to be pushed from the exit end 82 of the output orifice 82 through the aperture 24 of the disk 12.

The fusing anvil 88 can take the form of a heated solid aluminum plug attached to the sliding shuttle. Once the leading ends of the strands 26 project a short distance through the aperture 24 and beyond the rear wall 22 of the disk 12 into engagement with the fusing anvil 88, fusing of the leading strand ends commences as feeding of the strands continues until the strand connecting bead 30 is formed at the one end of the strands; then feeding is terminated. The multiple strands are fused into a single piece plastic bristle brush that is retractably and removably attached to the electrode disk 12 and will not accidentally separate from the disk.

Figure 6:
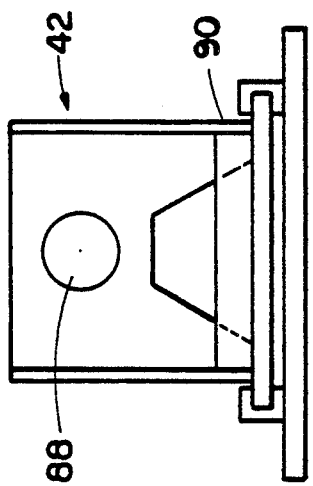
FIG. 6 is an enlarged view of a strand severing mechanism of the apparatus as seen along line 6—6 of FIG. 2.

The strand severing mechanism 44 of the apparatus 32 is disposed between the electrode disk support 36 and the strand feeding mechanism 38 at the location of a transverse guide slot 94 through the output orifice 82 which divides the latter into two separate parts. The severing mechanism 44 includes a block 96 mounted for vertical reciprocatory movement within the slot 94. The block 96 supports and vertically moves a cutting blade 98 along the disk support 36 for severing the strands 26 at a location spaced from their fused together leading ends 30 and displaced beyond the front end of the disk 12 so to define the opposite abrading end 28 of the brush 14. Springs 100 engage and bias the block 96 toward its upper retracted position above the strands, as shown in FIGS. 3, 3A and 6. The block 96 and blade 98 carried by the block can either be downwardly driven manually or by a solenoid.

In operation, the shuttle 90 is moved to the right and closed to hold the empty electrode disk 12 in the detent or countersink 60. The drive rollers 62,64 are then turned to feed the strands 26 through the disk 12 until the leading ends of the strands make contact with the fusing anvil 88. The rollers 62,64 continue to drive the strands into the fusing anvil 88 until the small melted bead 30 of plastic is formed at the anvil surface. The strands are then withdrawn from the fusing anvil 88 until the still melted plastic bead 30 is in contact with the electrode disk rear wall 50. This serves to create a very small but effective detent on the strands at the aperture 24 which keeps them from falling out of the disk. At this point, the cutting blade 98 is driven through the strands, cleanly cleaving the brush from the strand stock. The shuttle is then moved to the left and opened and the finished self-preparing electrode or monitor is removed. The same procedure is repeated for assembling additional electrodes.

It is thought that the invention and many of its attendant advantages will be understood from the foregoing description and it will be apparent that various changes may be made in the form, construction and arrangement thereof without departing from the spirit and scope of the invention or sacrificing all of its material advantages, the form hereinbefore described being merely a preferred or exemplary embodiment thereof.

What is claimed is:

1. A self-preparing electrode for sensing the electrical potential of a person's skin, comprising:
   (a) a conductive disk having a first side, a second side and a central aperture with said first side adapted to face the person's skin; and
   (b) a nonconductive multi-strand abrading brush frictionally mounted within said aperture in said disk and removable from said second side of said disk.

2. The electrode as recited in claim 1, wherein said disk defines a hollow cavity for receiving and holding an electrolyte cream for providing an electrically conductive coupling between said disk and the person's skin.

3. The electrode as recited in claim 1, wherein said strands of brush are a plastic monofilament material.

4. The electrode as recited in claim 1, wherein disk is composed of silver metal.

5. The electrode as recited in claim 2, wherein said disk has a frusto-conical shape and said cavity in said disk is open at a large diameter end of said disk.

6. The electrode as recited in claim 5, wherein said brush extends axially through said cavity to an abrading end of said brush disposed beyond said cavity at said large diameter end of said disk.

7. The electrode as recited in claim 5, wherein said cavity of said disk is closed at an opposite small diameter end of said disk except for said aperture.

8. The electrode as recited in claim 7, wherein said brush extends axially through said cavity to a fused end of said brush disposed through and beyond said aperture in said disk.

9. A self-preparing electrode for sensing the electrical potential of a person's skin, comprising:

(a) a conductive disk having a first side, a second side and a central aperture with said first side adapted to face a person's skin;

(b) a nonconductive multi-strand plastic abrading brush frictionally mounted within said aperture in said disk and removable from said second side of said disk;

(c) said disk defining a hollow cavity for receiving and holding an electrolyte cream for providing an electrically conductive coupling between said disk and the person's skin;

(d) said cavity in said disk being open at a large diameter end of said disk and closed at an opposite small diameter end of said disk except for said aperture;

(e) said brush extending axially through said cavity to an abrading end of said brush being disposed beyond said cavity at said large diameter end of said disk and to an opposite fused end of said brush being disposed through and beyond said aperture in said disk.

* * * * *